(12) United States Patent
Hall et al.

(10) Patent No.: US 7,341,749 B2
(45) Date of Patent: Mar. 11, 2008

(54) FLAVOPEREIRINE AND ALSTONINE COMBINATIONS IN THE TREATMENT AND PREVENTION OF PROSTATE CANCER

(75) Inventors: John L. Hall, New York, NY (US); Sylvie P. Beljanski, New York, NY (US)

(73) Assignee: Natural Source International Ltd., New York, NY (US)

( * ) Notice: Subject to any disclaimer, the term of this patent is extended or adjusted under 35 U.S.C. 154(b) by 306 days.

(21) Appl. No.: 11/132,183

(22) Filed: May 19, 2005

(65) Prior Publication Data

US 2005/0266107 A1 Dec. 1, 2005

Related U.S. Application Data

(60) Provisional application No. 60/572,098, filed on May 19, 2004.

(51) Int. Cl.
*A61K 36/00* (2006.01)
*A61K 36/89* (2006.01)
*A61K 31/535* (2006.01)
*A61K 31/50* (2006.01)

(52) U.S. Cl. .................. 424/725; 424/750; 514/222.8; 514/247

(58) Field of Classification Search ..................... None
See application file for complete search history.

(56) References Cited

U.S. PATENT DOCUMENTS 4,264,729 A    4/1981  Beljanski
5,519,028 A *  5/1996  Beljanski ..................... 514/285

FOREIGN PATENT DOCUMENTS

| EP | 0 059 817 B1 |   | 9/1985  |
|----|--------------|---|---------|
| FR | 2450607      | * | 11/1980 |
| JP | 57159712     | * | 10/1982 |

OTHER PUBLICATIONS

Schachter, M. Mirko Beljanski's Controversial Approach to Treating Cancer. Apr. 21, 2001, 3 page Internet article from http://mbschachter.com/mirko_beljanski.htm.*
Schachter, M. Mirko Beljanskis Innovative Approach to Helping Patients Suffering from Cancer, Chronic Viral Diseases and Autoimmune Conditions. Jul. 4, 2003 (as confirmed by the internet site WayBackMachine—attached herewith), 6 page internet article from http://mbschachter.com/mirko_beljanski.htm.*
Donald C. Malins et al.;"Models of DNA Structure Achieve Almost Perfect Discrimination between Normal Prostate, Benign Prostatic Hyperplasia (BPH), and Adenocarcinoma and Have a High Potential for Predicting BPH and Prostate Cancer" Proc. Natl. Acad. Sci.; vol. 94, (1997) pp. 259-264.
Mirko Beljanski et al.; "Oncotest: A DNA Assay System for the Screening of Carcinogenic Substances"; IRCS Medical Science; vol. 7, (1979); pp. 476; France.
Mirko Beljanski et al.; "Selective Inhibition of in Vitro Synthesis of Cancer DNA by Alkaloids of B-Carboline Class"; Experimental Cell Biology; vol. 7 (1982); pp. 79-87; S.Karger,Basel; Switzerland.
M. Beljanski et al.; "Three Alkaloids as Selective Destroyers of the Proliferative Capacity of Cancer Cells"; IRCS Medical Science; vol. 12, (1984); pp. 587-588; France.
M. Beljanski et al. "Three Alkaloids as Selective Destroyers of Cancer Cells in Mice"; Oncology; vol. 12 (1986); pp. 198-203; S. Karger AG, Basel.
Mirko Beljanski et al.; "The Selective Anticacer Agents PB-100 and BG-8 are Active Against Human Melanoma Cells, but Do Not Affect Non Malignant Fibroblasts"; International Journal of Oncology vol. 8 (1996); pp. 1143-1148; France.
Mirko Beljanski; "The Anticancer Agent PB-100, Selectively Active on Malignant Cells, Inhibits Multiplication of Sixteen Malignant Cell Lines, Even Multidrug Resistant"; Genetics and Molecular Biology, vol. 23 (2000); pp. 29-33; FRANCE.
Donal C. Malins et al.; "Cancer-Related Changes in Prostate DNA as Men Age and Early Identificatiion of Metastasis in Primary Prostate Tumors"; Biochemical Oncology Program, vol. 100, Apr. 29, 2003; pp. 5401-5406.
Mirko Beljanski et al.; "Abstracts for the First Congress of the European Association for Neuro-Oncology"; Journal of Neuro-Oncology; vol. 21 (1994); p. 62; France.
M. Beljanski et al.; "A Potent and Selective Inhibitor of Human BCNU Resistant Glioblastoma Cell Multiplication"; Anticancer Research, vol. 13 (1993); pp. 2301-2308; France.
Mirko Beljanski et al.; "The Anticancer Agent PB-100 Concentrates in the Nucleus and Nucleoli of Human Glioblastoma Cells but Does Not Enter Normal Astrocytes"; International Journal of Oncology; vol. 7 (1995); pp. 81-85; FRANCE.
Mirko Beljanski; A New Approach to Cancer Therapy; pp. 86-108; FRANCE.

\* cited by examiner

*Primary Examiner*—Christopher R. Tate
(74) *Attorney, Agent, or Firm*—Venable LLP; Thomas G. Wiseman

(57) ABSTRACT

A method and composition for preventing prostate cancer and/or reducing PSA levels and/or alleviating the symptoms of BPH (Benign Prostatic Hyperplasia) or PIN (prostatic intraepithelial neoplasia) by administration of an effective amount of a mixture of flavopereirine and alstonine. A method and composition for treating low-grade prostate cancer and preventing the onset of metastatic disease and/or reducing the doubling time of PSA levels in men with positive biopsies showing relatively low Gleason scores and morphologies characteristic of non-invasive, slow-progressing prostate cancer. The flavopereirine and alstonine can be in the form of natural extracts derived from *Pao Pereira* and *Rauwolfia Vomitoria*, respectively. Alternatively, these two active compounds can be administered in purified form. The composition can be in included in a kit along with instructions for use in a treatment regimen.

23 Claims, 7 Drawing Sheets

PARP CLEAVAGE

CASPASE-3 ACTIVITY

TUNEL STAINING

CONTROL

TUNEL STAINING 50 mg/kg PAO

TUNEL STAINING 20 mg/kg PAO

TUNEL STAINING 10 mg/kg PAO

FLAVOPEREIRINE AND ALSTONINE COMBINATIONS IN THE TREATMENT AND PREVENTION OF PROSTATE CANCER

FIELD OF INVENTION

This invention is in the field of the prevention and treatment of prostate cancer. More specifically, this invention relates to the use of flavopereirine and alstonine combinations in preventing and treating prostate cancer.

BACKGROUND OF THE INVENTION

Prostate cancer is the most prevalent cancer in men. Diagnosis is based on a tissue biopsy, microscopic examination of a small section of the prostate. When the biopsy contains cancerous cells the therapeutic options generally include radio- and chemotherapies, hormone treatments as well as surgical removal of the prostate gland. It is well known that these treatments are frequently devastating for the patient and notwithstanding these therapies mortality from prostate cancer is high.

There is an urgent need for agents that prevent the advancement of prostate cancer. Indeed, of the approximately one million prostate biopsies performed in this country every year, by far the majority are negative. Yet these men suffer a range of symptoms associated with elevated PSA levels and benign prostatic hyperplasia affecting urinary and sexual function. These large groups of men with BPH (Benign Prostatic Hyperplasia) or elevated PSA, or with PIN (prostatic intraepithelial neoplasia), but with negative biopsies, are precancerous: they are at high risk of developing an aggressive prostate cancer and there have been no effective preventive treatments. Agents that forestall or significantly delay the onset of cancer in this population have remarkable therapeutic value.

Another large population of men is diagnosed with prostate cancer, but their biopsies reveal a low-grade form of the disease. This group is in the well-known 'watchful waiting' or 'active surveillance' category and when the rate of increase in their PSA levels is relatively rapid they are subject to the therapeutic interventions cited above. These large groups of men—those in watchful waiting and those with shorter PSA doubling times need agents that subdue their cancers, slow the rate of PSA increase, and prevent the progression of their cancers to a higher grade and more aggressive form. Such an agent would fill a major vacuum in healthcare for men.

A third population of men undergo one of the traditional therapies in which case their recovery is assessed by monitoring the rate of change or the doubling time of their PSA levels which serve as an indicator of how rapidly their cancer is likely to return. An agent that is effective in reducing PSA levels and in moderating PSA doubling times could be used in combination with traditional therapies to help prevent the recurrence of prostate cancer thus significantly extending the life of this population of cancer patients.

SUMMARY OF THE INVENTION

The present invention includes compositions and methods for alleviating or avoiding the onset of the symptoms associated with prostate cancer, for treating low-grade prostate cancers and preventing their progression to more advanced cancers, and for decreasing PSA doubling times and thus preventing or delaying metastatic prostate cancer.

The composition includes a mixture of flavopereirine and alstonine. Flavopereirine and alstonine are present in defined ratios relative to each other. The flavopereirine and alstonine may be present as plant extracts. The extract containing flavopereirine is derived from *Pao Pereira* and the extract containing alstonine is derived from *Rauwolfia Vomitora*. The extract of flavopereirine to the extract of alstonine ratio is about 3-4:1 and is based on the active ingredients being in extract form, i.e. *Pao Pereira* extract to *Rauwolfia Vomitora* extract. Alternatively the flavopereirine and alstonine may be present in purified chemical form, i.e. a combination of synthetic flavopereirine and synthetic alstonine. It is expected that the ratio will vary somewhat depending on the purity of the active ingredients in the case of the active ingredients being in extract form. The amounts are sufficient to induce apoptosis and disruption of the cell cycle and DNA damage response pathways in prostate cancer cells.

Any conventional modes of administration for compounds of this type are envisioned. Currently, oral administration is contemplated. Typical modes of this type would include tablets and capsules. These could be packaged in kit form with written instructions to facilitate a treatment regimen.

The population envisioned for treatment with the flavopereirine and alstonine mixture falls into three groups: 1) those subjects thought to be susceptible to prostate cancer; 2) those subjects with low-grade forms of prostate cancer with both low and high PSA doubling times; and 3) those subjects combining treatment with traditional medical therapies (specifically surgery, radiation, and cryo- and/or chemotherapy) Population number one could include such high-risk groups as males having a high PSA count, symptoms of BPH (Benign Prostatic Hyperplasia) or with PIN (prostatic intraepithelial neoplasia). This group will have negative biopsies and would be considered precancerous. The amount of the mixture is sufficient to alleviate the symptoms of BPH (Benign Prostatic Hyperplasia) or to lower elevated PSA levels over time. Population number two will have been diagnosed with prostate cancer and thus will be likely to have positive biopsies, but have non-aggressive tumors characterized by lower Gleason scores. This population will include men with relatively low rates of PSA increase as well as men with higher rates of PSA increase. The amount of the mixture is sufficient to slow the progression of prostate cancer to a more aggressive stage and to lower PSA levels and PSA doubling times. Population number three will have or will be undergoing some form of prostate cancer therapy (surgery, radiation, cryo- or chemotherapy). Used in combination with these therapies the amount of the mixture is sufficient to lower PSA doubling times.

The invention also includes a novel combination of these two extracts in relative amounts to prevent prostate cancer or alleviate symptoms of BPH, especially in precancerous men including men diagnosed with prostatic intraepithelial neoplasia (PIN). The extracts exert beneficial effects without the side effects normally associated with anti-cancer treatments. e Precancerous cell that are becoming cancerous are selectively killed by the mixture and the normal cells are left unaffected.

The invention also includes a method of preventing prostate carcinogenesis in patients having a precancerous precursor of prostate adenocarcinoma, elevated PSA, and Benign Prostatic Hyperplasia, but who do not as yet have prostate cancer. The invention further includes a method for reducing PSA levels and/or alleviating the symptoms of BPH.

The invention also includes a method of treating men with localized (non-metastatic) prostate cancer to prevent the development of higher-grade tumors and more aggressive disease. The cancer cells are selectively killed by the mixture and the normal cells are left unaffected.

The invention also includes a method of treating men with both long and short PSA doubling times and of lengthening the PSA doubling times. This treatment will help maintain the 'watchful waiting' status of men with long PSA doubling times and help prevent the onset of more aggressive or metastatic disease in men with short PSA doubling times.

The invention further provides a method of administering to an individual an orally effective dosage of the extracts in capsule or tablet form.

The invention provides a method for suppression or inhibition of prostate carcinogenesis, reduction of PSA levels, and reduction of the symptoms of BPH by administration of the preventive agent that consists of a combination of natural extracts derived from *Pao Pereira* and *Rauwolfia Vomitora*.

The invention provides a mechanism of action for the preventive agent by induction of apoptosis and disruption of cell cycle and DNA damage response pathways in cancer cells. At optimal concentrations this mechanism is selective for cancer cells and it also contributes to the effectiveness of the preventive agent in reducing PSA levels and the symptoms of BPH.

DESCRIPTION OF THE INVENTION

Overview

Figure 1A:
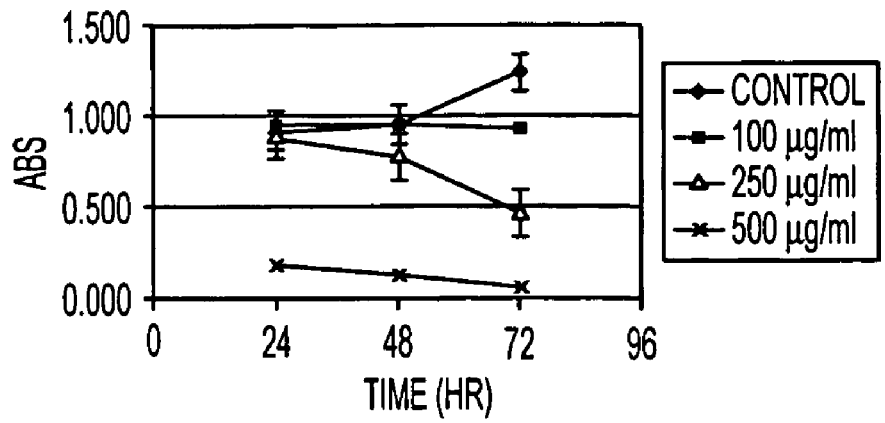
FIG. 1 shows the results of LNCaP cell growth analyses following treatment with *Rauwolfia* and *Pao* extracts.

The present invention builds on the scientific research of M. Beljanski who first developed these extracts and demonstrated their selective activity against cancer cells in laboratory experiments and in animal studies. Beljanski provided evidence that the toxicity of these compounds is based on their interaction with the destabilized DNA that he found to be a primary characteristic of cancer cells.

The work described herein supports the correlation of the extent of DNA damage in prostate cells with cancer of the prostate; this also supports the specific diagnosis of a precancerous condition of the prostate. Also described is work demonstrating the mechanism of action involves induction of apoptosis and disruption of the cell cycle and DNA damage response pathways in prostate cancer cells. This is shown both in tissue culture and in an animal xenograft model. Uncovering the differential mechanisms of action of flavopereirine and alstonine supports the concept of using a specific combination of the extracts to obtain an enhanced therapeutic effect.

The classification of an intermediate or precancerous stage of prostate DNA damage indicated that these compounds would exert their toxic effect specifically on precancerous cells that are in transition to a cancerous state thereby preventing cancer in high-risk men and answering the urgent need of a very large patient population. These compounds also exert their toxic effect on cancer cells thereby preventing advancement to a higher grade and more aggressive form of prostate cancer.

Discovery of the Anti-Cancer Activity of *Pao Pereira* and *Rauwolfia Vomitoria* Extracts.

The extract from *Pao Pereira* is prepared according to the protocol in U.S. Pat. No. 5,519,028. The extract from *Rauwolfia Vomitoria* is prepared according to the procedure in European Pat. No. EP-A-0 059 817. This procedure includes a partial purification step that eliminates toxic compounds (e.g. reserpine) from the product.

The biochemical activity of these two extracts was first analyzed in an in vitro assay called the Oncotest (U.S. Pat. No. 4,264,729). This test was originally designed to screen compounds for their carcinogenic potential and is based on differences in the secondary structure of DNAs isolated from cancer cells and from normal cells (Beljanski, *IRCS Med. Sci.* 1979. 7:476). Relative to purified normal DNA, purified cancer cell DNA exhibits greater chromicity (absorption of UV light) and greater activity when used as a template for in vitro DNA synthesis (Beljanski et al., *Expl. Cell. Biol.*, 1981. 49:220-231. This indicates that the hydrogen bonds in the double helix of cancer DNA are reproducibly disrupted resulting in openings or loops that increase UV absorption and enhance enzymatic activity in vitro. This fundamental difference in structure, the greater strand separation characteristic of cancer DNA, was referred to as DNA destabilization (Beljanski, Proceedings of the international seminar: Traditional Medicine: a Challenge to the 21$^{st}$ Century. 1992. Oxford and IBH Publishing Co.)

When known carcinogens are added to the Oncotest they promote a small increase in DNA synthesis with normal templates, but a much higher increase (5 to 10 fold) in DNA synthesis with cancer templates (Beljanski et al. Third NCI-EORTC Symposium on new drugs in cancer therapy. 1981. Institut Bordet, Bruxelles). Such compounds are thought to act by further opening the already comparatively relaxed structure of the cancer DNA thereby enhancing the access of enzymes to the template and enabling more DNA to be synthesized.

When the *Pao* and *Rauwolfia* extracts are used in the Oncotest they have the opposite affect of a carcinogen: chromicity is diminished and DNA synthesis from cancer DNA templates is inhibited (Beljanski, *Expl. Cell. Biol.* 1982. 50: 79-87). Biochemical analysis of the extracts, including DNA binding assays, identified the active compounds as flavopereirine (in *Pao Pereira*) and alstonine (in *Rauwolfia Vomitoria*). Since the inhibitory effects shown by the extracts and their respective compounds is specific for cancer DNA, since there is no effect on normal DNA, and since very few of the hundreds of compounds that were screened gave these results, these extracts and the corresponding active compounds were further assessed for their potential as anti-cancer agents.

The extracts were subjected to a long series of tests to examine their effect on cultured cancer cells (Beljanski et al., *IRCS Med. Sci.* 1984. 12:587-588), on animals with various kinds of cancer (Beljanski et al., Oncology, 1986. 43:198-203), and ultimately in numerous human case studies. The extracts showed several consistent and noteworthy properties. First, at optimal concentrations, they stopped the proliferation of cancer cell lines maintained in the laboratory, while sparing healthy cells. They were toxic to cancer cells in mice, but did no harm to the mice. They have proven to have anti-cancer effects on a range of human malignancies, but have shown no significant side effects. The activity of these extracts is selective to cancer DNA, to cancer cells, and to the tumors of organisms with cancer. There is evidence that this selectivity is due, in part, to their preferential entry into cancer cells because of changes that occur in the outer membranes of these cells (Beljanski et al. *International Journal of Oncology*, 1996. 8:1143-1148). In the course of these experiments, the activity of the *Pao Pereira* extract (flavopereirine) (Beljanski, *Genetics and Mol. Biol.*, 2000. 23, 1:29-33) and the *Rauwolfia Vomitoria* extract (alstonine) (unpublished data) were shown to inhibit the multiplication of a human prostate cancer cell line (PC3) to a similar extent. This result is significant in the context of the present invention because it demonstrates that both of the active compounds in the mixture are effective against cancer cells like PC-3 that do not respond to hormones.

For the Oncotest, cancer DNA was isolated from a range of cancerous tissues or cells including breast, lung, ovary, neurocarcinoma, Ehrlich ascites tumor cells, KB and HeLa and L cells. Normal DNA was isolated from healthy breast, lung, ovary, brain, primary kidney, Vero cells, or SIRC cells in culture. Cell lines exposed to *Pao Pereira* extract included: u251, CCF-STTG-1 SW 1088 and C6 (brain); LoVo, CaCo-2 (colon); Sk-Hep 1 (liver); A498 (kidney); G-361 (skin); Es 2, Sw 626 (ovary); ZR-75-1, MCF-7 (breast); MIA PaCa2 (pancreas); PC3 (prostate); and TT (thymus). Normal cell lines tested with *Pao Pereira* include CRL 1656 (brain); CCD-18Co (colon); Clone 9 (liver); NRK-49F (kidney); and CCD-97Sk (skin). A summary of anecdotal information concerning the use of the extracts for treating human cancer patients can be found in Beljanski, Mirko Beljanski ou La Chronique d'une "Fatwa" Scientifique, 2001, EVI Liberty Corp.

DNA Destabilization in Cancer Cells

Recent studies by Malins et al. (Cancer related changes in prostate DNA as men age and early identification of metastasis in primary prostate tumors. *Proc. Natl. Acad. Sci.* Apr. 29 2003 100(9): 5401-5406) using Fourier Transform Mass Spectroscopy have shown that the DNA in prostate cancer cells is indeed different from the DNA of normal prostate cells. Malins et al. refer to the difference as an increase in disorder in the cancer DNA relative to normal DNA and these changes correlate with age and apparently with exposure to carcinogens. Malins et al were also able to reproducibly detect an interim stage of disorder reflecting a precancerous condition of the prostate (Malins et al. Models of DNA structure achieve almost perfect discrimination between normal prostate, benign prostatic hyperplasia (BPH), and adenocarcinoma and have a high potential for predicting BPH and prostate cancer. *Proc. Natl. Acad. Sci.* 7 Jan. 1997; 94 (1): 259-264). This precancerous condition appears to correspond to the clinical condition known as prostatic intraepithelial neoplasia (PIN).

Malins et al. report that the presence of carcinogens in the prostate leads to the production of free radicals that physically damage the DNA yielding 'potentially billions of altered structures.' Many of these alterations will affect the hydrogen bonds that stabilize the DNA duplex. This could produce the openings in the helix structure reported by Beljanski.

Figure 1B:
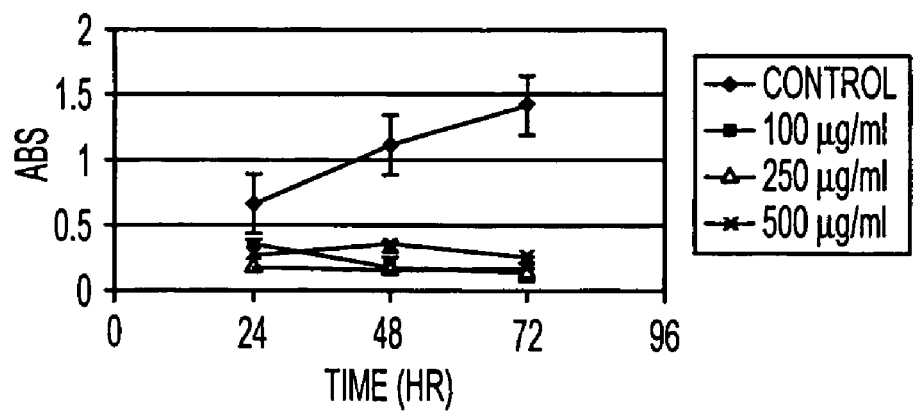

Novel Data Supporting the Application of *Pao Pereira* and *Rauwolfia* Extracts for the Prevention of Prostate Cancer 1. Induction of Apoptosis: The Primary Mechanism of Action of Flavopereirine Flavopereirine and alstonine are structurally related alkaloids of the beta-carboline class. There is evidence that they enter the relatively open strands of the DNA in cancer cells and intercalate between adjacent nucleotides where their presence apparently interferes with the metabolism of DNA (Calvez, Flavopereirine is an intercalating agent for non-supercoiled DNA, Cancer Detection and Prevention 1998; 22(Supplement 1)). In effect, the destabilized DNA of the cancer cell is a target of these alkaloids and the end result is cell death. The toxicity for cancer cells was confirmed in new experiments showing that both the *Pao* and *Rauwolfia* extracts inhibit the growth of LNCaP prostate cancer cells in tissue culture (FIG. 1). Moreover, these extracts exhibited significantly higher toxicity for LNCaP cells than for a primary culture of normal prostate cells (Data not shown).

Figure 2A:
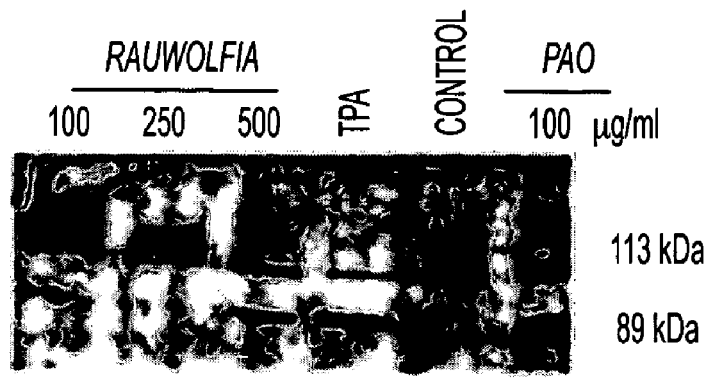
FIG. 2 shows the induction of apoptosis in LNCaP cells by both *Rauwolfia* and *Pao* extracts after 24 hours in terms of PARP cleavage and Caspase-3 activity.
Figure 2B:
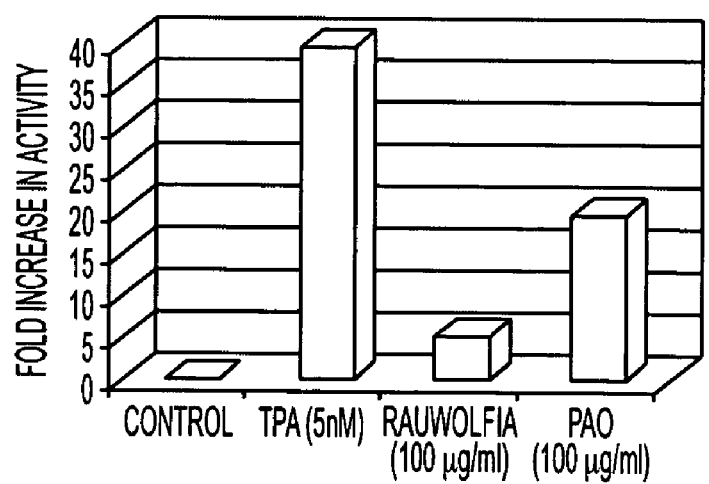

Our recent experiments have also shown that the primary mechanism of action of flavopereirine is the induction of apoptosis whereas alstonine has a relatively minor effect in the induction of this pathway Both the *Pao Pereira* extract and the *Rauwolfia Vomitoria* extract triggered apoptosis in the prostate cancer cell line LNCaP as determined by cleavage of PARP and induction of Caspase-3 [FIG. 2], but the effect of the *Rauwolfia* extract was considerably less than the effect of to *Pao* extract.

Apoptosis—also called programmed cell death—is a built-in biochemical pathway that triggers a cell to commit suicide. This pathway is normally used during development (e.g. in the development of the nervous system), by the immune system to protect the body from altered cells (e.g. cells infected by a virus), and as a cellular reaction to DNA damage (e.g. if not destroyed these cells can become cancerous). In many cancers, including many prostate cancers, the mechanism for inducing apoptosis is defective so cells that should normally be committing suicide survive and grow to form a tumor. Numerous cancer therapies actually function by inducing apoptosis in certain types of cancer cells.

The induction of apoptosis is a central theme in the prostate cancer research community and the fact that the *Pao Pereira* and (to a significantly lower degree *Rauwolfia Vomitoria*) extracts exhibit this effect makes them extremely attractive as potential anti-prostate cancer agents.

Figure 3:
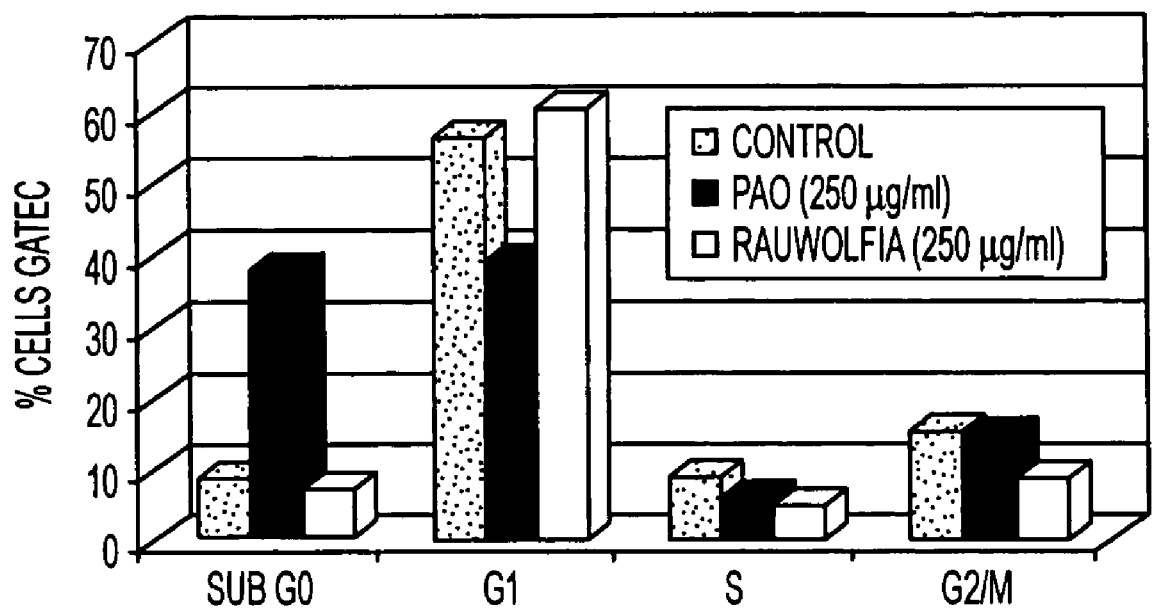
FIG. 3 shows cell cycle analysis by FACS.

2. Potential for Synergistic Action of Flavopereirine and Alstonine Based on Differential Effects on the Apoptotic Pathway, on the Cell Cycle, and on the DNA Damage Response Pathway Although both extracts induce apoptosis and are toxic for prostate cancer cells, analysis of their action in the cell cycle by fluorescence activated cell sorting revealed different effects. As shown in FIG. 3, the *Pao Pereira* extract causes accumulation of LNCaP cells in SubG0 whereas *Rauwolfia Vomitoria* hinder progression of the cells from G1 to S. This result highlights a difference in the mechanism of action of the two extracts whose biochemical basis remains to be determined, though it is presumably based on the difference in the physical structures of flavopereirine and alstonine. One possibility is that they may induce apoptosis by different pathways (e.g. p53-dependent and p53-independent) and another is that they may function with somewhat different kinetics. Regardless of the reason, this difference in activity has therapeutic value: combinations of the two extracts have the potential to act in complementary fashion, that is, they are potentially synergistic in their anti-cancer effects. Combination therapies are often used in cancer treatment and are widely considered to offer significant advantages over the use of a single anti-cancer agent alone.

To further explore the effect of these two extracts on prostate cancer cells a series of microarray assays were performed using arrays containing three different sets of human genes belonging to three different biochemical pathways: apoptosis, cell cycle, and DNA damage. In each case that RNAs for the assays were isolated from LNCaP cells that had been exposed to the extracts for 24 hours. The data obtained from these microarray experiments are referred to collectively as Table I. See Annex. Note that real time PCR was used to spot check the validity of the changes observed in these assays While the process of analyzing these data and synthesizing coherent descriptions of the effect of the *Pao* and *Rauwolfia* extracts on these complex pathways is ongoing and will require additional experiments, several observations can be made highlighting the fact that the two extracts induce different responses in all three microarrays. For example, in the DNA damage response array the *Pao* extract has a potentially significant effect on the expression of fourteen (14) genes (shown in bold) whereas the *Rauwolfia* extract has a potentially significant response on thirty (30) transcripts. Closer inspection reveals that both extracts have significant effects on the expression of just four common genes (ATM, DDIT3, ERCC1, and PDCD8). Even more remarkable is that of the four genes affected by both extracts only two are affected in the same way: DDIT3 and ERCC1 are both up-regulated. Analysis of the two other microarrays also reveals divergent results for the *Pao Pereira* and *Rauwolfia Vomitoria* extracts strongly substantiating the use of these extracts in combination in order to obtain their complementary effects.

3. Flavopereirine and Alstonine are Active Against Prostate Cancer Tumors in a Xenograft Animal Model The ability of human tumors to grow as xenografts in athymic mice (e.g., Balb/c, nu/nu) provides a useful in vivo model for studying the biological response to therapies for human cancers. Since the first successful xenotransplantation of human tumors into athymic mice, many different human tumor cell lines (e.g., mammary, lung, genitourinary, gastro-intestinal, head and neck, glioblastoma, bone, and malignant melanomas) have been transplanted and successfully grown in nude mice. The use of this system enabled analysis of the activity of the compounds of the present invention on a prostate cancer xenograft of LNCaP cells in a mammal—a better model for humans than cell-based assays. A number of tests may be used to determine the level of activity, specificity and effect of the compounds and in this case tumor volume and immunohistochemistry were the endpoints.

Figure 4A:
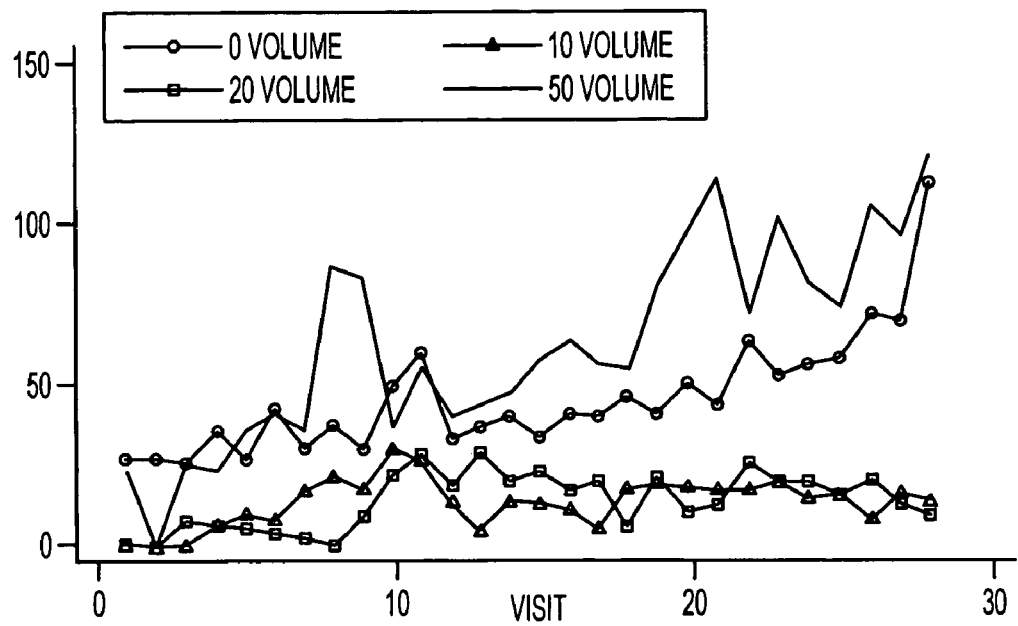
FIGS. 4 (A and B) shows the results of a prostate cell tumor growth experiment.
Figure 4B:
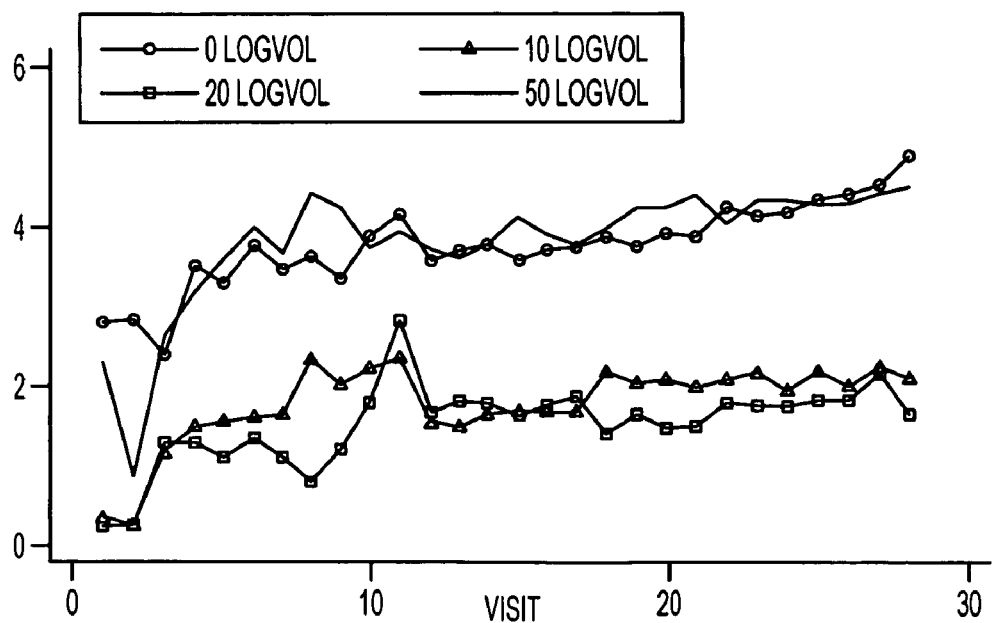
Figure 5A:
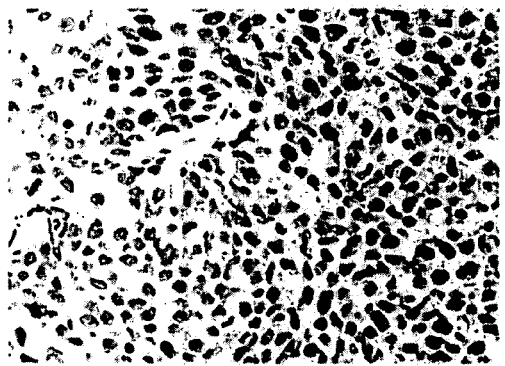
FIG. 5 shows the results for the TUNEL staining assay.
Figure 5B:
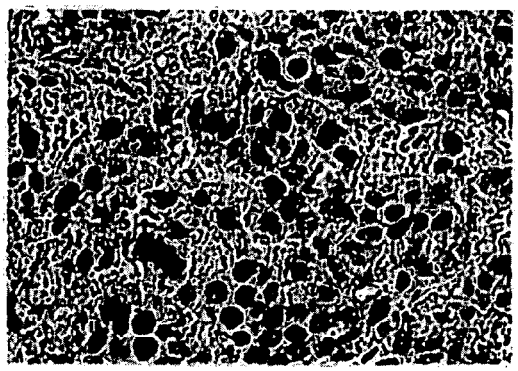
Figure 5C:
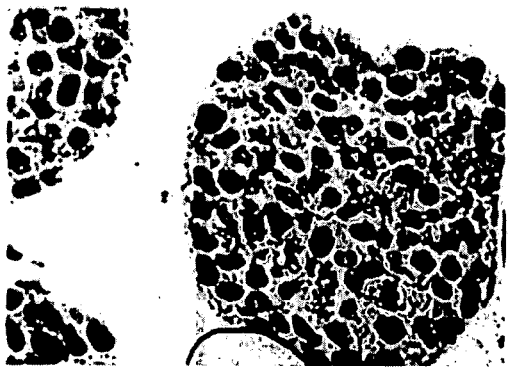
Figure 5D:
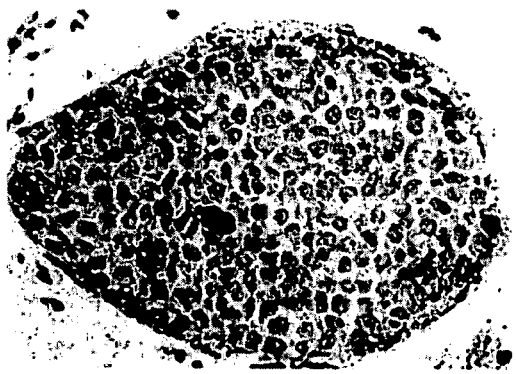
Figure 6:
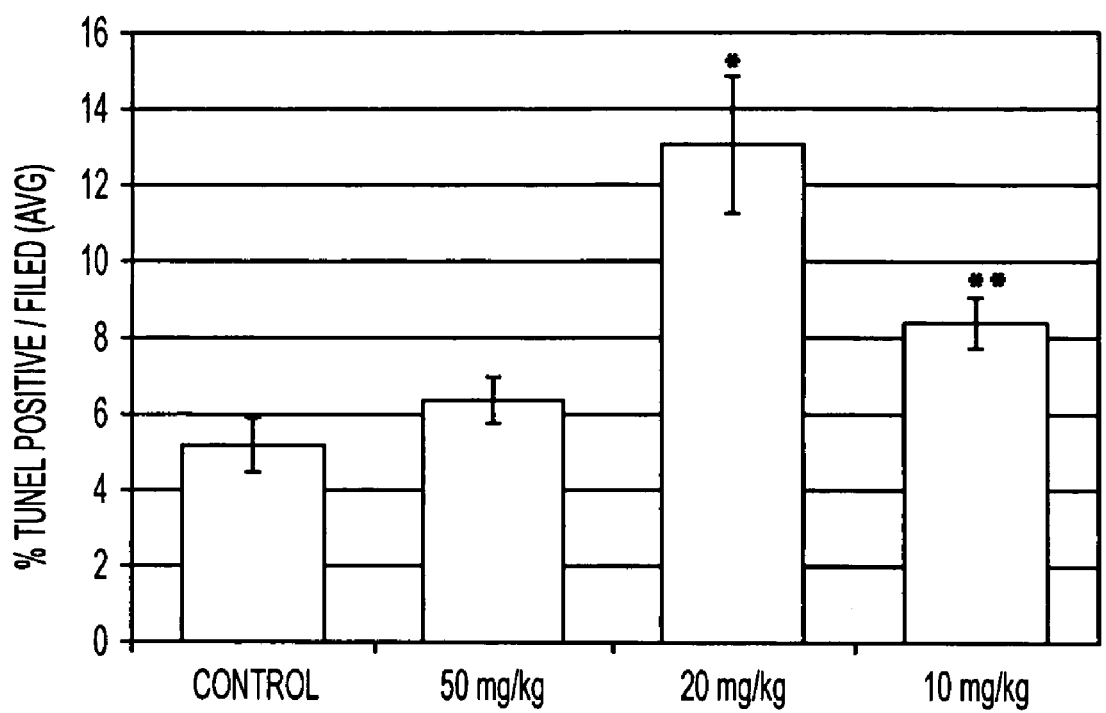
FIG. 6 shows the corresponding statistical data for the TUNEL staining assay.
Figure 7:
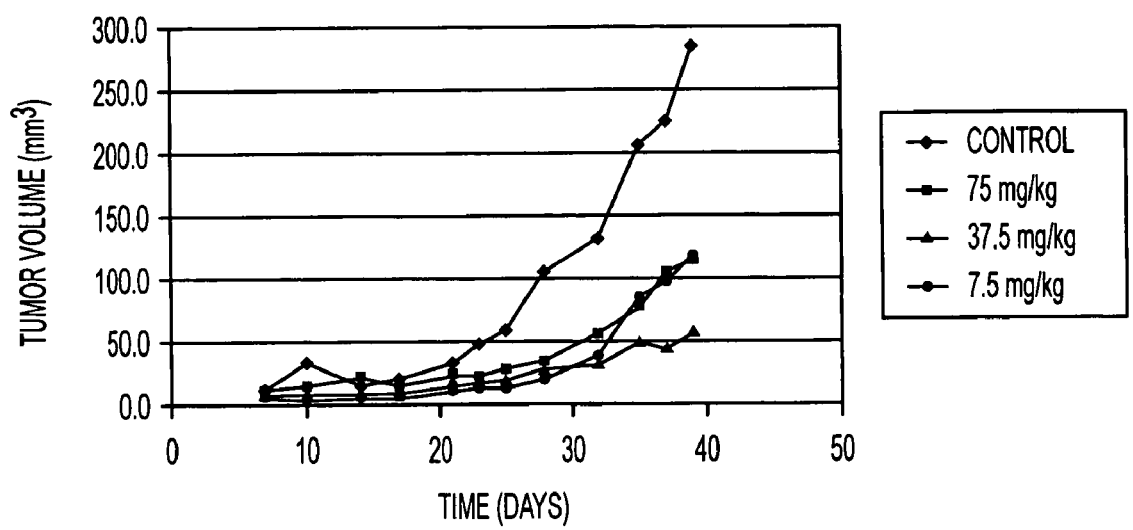
FIG. 7 shows the experimental results illustrating the suppression of LNCap tumor xenograft growth by *Rauwolfia*.

A graph of the results of the xenograft experiment using the *Pao Pereira* extract, with measurement of tumor size (cubic millimeters) plotted against time (days), are shown if FIG. 4A. Daily doses of 10 and 20 mg/kg of *Pao Pereira* extract caused a statistically significant reduction in tumor volume compared to control animals and to animals treated with 50 mg/kg per day. The log transformation shown in FIG. 4B clearly shows that the results fall into two classes. A graph of the results of the xenograft experiment using the *Rauwolfia Vomitoria* extract is shown in FIG. 7. In this case all three doses of the extract caused statistically significant reduction in tumor volume relative to the controls [$p<0.0001$)]. Finally, data from two immunohistochemical assays using sections of the tumors removed from the animals confirmed that the mechanism of action of *Pao* is the induction of apoptosis which is dosage dependent. The results for the TUNEL staining assay are shown in FIG. 5 and the corresponding statistical data are shown in FIG. 6. Consistent results were obtained in the BrdU staining assay [Data not shown]. Similar immunohistochemistry for the *Rauwolfia Vomitoria* experiment is currently underway.

The dramatic effect of these extracts in reducing tumor volume must also be considered in light of the remarkable fact that the health of the animals in these experiments is not otherwise compromised in any adverse way. For example, the weights of treated and control mice show no significant differences throughout the course of the experiment. The anti-prostate cancer effects of both extracts together with the absence of negative side effects provide a strong scientific basis for the claims described in the present invention.

Formulation and Administration

The flavopereirine and alstonine combinations can be formulated as pharmaceutical compositions. The compositions can be included in pharmaceutical kits. Depending on the subject to be treated, the mode of administration, and the type of treatment desired—e.g., prevention, prophylaxis, therapy; the flavopereirine and alstonine combinations are formulated in ways consistent with these parameters. A summary of such techniques is found in Remington's Pharmaceutical Sciences, latest edition, Mack Publishing Co., Easton, Pa.

In general, for use in treatment or prophylaxis, the mixture of flavopereirine and alstonine may be used alone or in combination with other chemotherapeutic agents compounds. The mixture of flavopereirine and alstonine can be administrated singly or in combination with other pharmaceutically active components, and in single or multiple administrations. The mixture formulation may be prepared in a manner suitable for systemic administration. Systemic formulations include those designed for injection, e.g. intramuscular, intravenous or subcutaneous injection, or may be prepared for transdermal, transmucosl, or oral administration. The formulation will generally include a diluent as well as, in some cases, adjuvants, buffers, preservatives and the like. The flavopereirine and alstonine mixture can be administered also in liposomal compositions or as microemulsions using conventional techniques.

If orally administered, the flavopereirine and alstonine combination of the invention can be protected from degradation in the stomach using a suitable enteric coating.

The manner of administration and formulation of the mixture useful in the invention will depend on the nature of the condition, the severity of the condition, the particular subject to be treated, and the judgment of the practitioner, formulation will depend on mode of administration As the mixture of the invention involve small molecules, it is conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 1%-99% of the total formulation, but wide variation is permitted depending on the carrier. Suitable carriers include sucrose, pectin, magnesium stearate, lactose, peanut oil, olive oil, water, and the like.

The mixture may also be administered by injection, including intravenous, intramuscular, subcutaneous or intraperitoneal injection. Typical formulations for such use are liquid formulations in isotonic vehicles such as Hank's solution or Ringer's solution.

Suitable alternative formulations also include liposomal formulations, slow-release formulations, and the like.

Any suitable formulation may be used. A compendium of art-known formulations is found in Remington's Pharmaceutical Sciences, latest edition, Mack Publishing Company, Easton, Pa. Reference to this manual is routine in the art.

The dosages of the compounds of the invention will depend on a number of factors which will vary from patient to patient.

Oral dosage forms include capsules and tablets. Capsule or tablets can be easily formulated and can be made easy to swallow. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

As noted above the flavopereirine and alstonine mixture can be included in a kit form. The mixture would be formulated for use as a pharmaceutical. The kits can comprise one or more containers containing the pharmaceutical form of the mixture, which comprises a therapeutically effective amount of the mixture in unit dosage form. Such kits can further include, if desired, one or more of various conventional pharmaceutical kit components, such as, for example, containers with one or more pharmaceutically acceptable carriers, additional containers, etc., as will be readily apparent to those skilled in the art. Instructions, such as printed instructions for example, either as inserts or as labels, the instruction indicating quantities of the components to be administered, guidelines for administration, and/or guidelines for further mixing with additional components, can also be included in the kit.

All of the references referred to above are hereby incorporated by reference in their entirety.

While the invention has been described in detail, and with reference to specific embodiments thereof, it will be apparent to one of ordinary skill in the art that various changes and modifications can be made therein without departing from the spirit and scope thereof.

REFERENCES CITED

Beljanski, M., Bourgarel, P., Beljanski, M. S. Correlation between in vitro DNA Synthesis, DNA Strand Separation and in vivo Multiplication of Cancer Cells. *Expl. Cell. Biol.*, 1981. 49: pp. 220-231.

Beljanski, M., A New Approach to Cancer Therapy. Proceedings of the international seminar: Traditional Medicine: a Challenge of the 21st Century, Nov. 7-9, 1992, Calcutta. Oxford and IBH Publishing Co. (ed. in chief Biswapati Mukherjee).

Malins, D. C., Polissar, N. L., Gunselman, S. J. Models of DNA structure achieve almost perfect discrimination between normal prostate, benign prostatic hyperplasia (BPH), and adenocarcinoma and have a high potential for predicting BPH and prostate cancer. *Proc. Natl. Acad. Sci.* Jan. 7, 1997; 94 (1): 259-264.

Malins, D. C., Johnson, P. M., Barker, E. A., Polissar, N. L., Wheeler, T. M., Anderson, K. M. Cancer-related changes in prostate DNA as men age and early identification of metastasis in primary prostate tumors. *Proc. Natl. Acad. Sci.* 2003 Apr. 29; 100 (9): 5401-5406.

Beljanski, M., Oncotest: a DNA assay system for the screening of carcinogenic substances. *IRCS Medical Science.* 1979. 7: p. 476.

Beljanski, M., Le Goff, L., Beljsanski, M. S. Differential susceptibility of cancer and normal DNA templates allows the detection of carcinogens and anticancer drugs. Third NCI-EORTC Symposium on new drugs in cancer therapy. 1981. Institut Bordet, Bruxelles.

Beljanski, M., Beljanski, M. S. Selective Inhibition of in vitro Synthesis of Cancer DNA by Alkaloids of β-Carboline Class. *Expl. Cell. Biol.* 1982. 50: pp. 79-87.

Beljanski, M., Beljanski, M. S. Three alkaloids as selective destroyers of the proliferative capacity of cancer cells. *IRCS Med. Sci.* 1984. 12: pp. 587-588.

Beljanski, M., Beljanski, M. S. Three Alkaloids as Selective Destroyers of Cancer Cells in Mice. Synergy with Classic Anticancer Drugs. *Oncology,* 1986. 43: pp. 198-203.

Beljanski, M., Crochet, S., Beljanski, M. S. PB100: A Potent and Selective Inhibitor of Human BCNU Resistant Glioblastoma Cell Multiplication. *Anticancer Research,* 1993. 13: pp. 2301-2308.

Beljanski, M., Crochet, S. Selective inhibitor (PB-100) of human glioblastoma cell multiplication. *Journal of Neuro-Oncology.* 1994. 21: p. 62.

Beljanski, M., Crochet, S. The selective anticancer agents PB-100 and BG-8 are active against human melanoma cells, but do not affect non-malignant fibroblasts. *International Journal of Oncology.* 1996. 8:1143-1148.

Beljanski, M., Crochet, S., The anticancer agent PB-100 concentrates in the nucleus and nucleoli of human glioblastoma cells but does not enter normal astrocytes. *International Journal of Oncology.* 1995. 7:81-85.

Beljanski, M., The anticancer agent pB-100, selectively active on malignant cells, inhibits multiplication of sixteen malignant cell lines, even multidrug resistant. *Genetics and Mol. Biol.* 2000. 23,1:29-33.

Incorporation by Reference the extent necessary to understand or complete the disclosure of the present invention, all publications, patents, and patent applications mentioned herein are expressly incorporated by reference therein to the same extent as though each were individually so incorporated.

What is claimed is:

1. A method for treating prostate cancer or delaying its onset comprising administering an effective amount of a mixture of flavopereirine and alstonine to a subject having a precursor to prostate cancer or prostate cancer for a time sufficient to slow the progression of prostate cancer to a more aggressive stage, lower PSA levels or lower PSA doubling times and wherein the flavoperine and alstonine are present in the mixture in a ratio of about 3-4 to one, respectively.

2. The method of claim 1 wherein the mixture is formed from natural extracts containing flavopereirine and/or alstonine.

3. The method of claim 2 wherein the natural extracts are from *Pao Pereira* and *Rauwolfia Vomitora*.

4. The method of claim 3 wherein the *Pao Pereira* extract contains flavopereirine and the *Rauwolfia Vomitoria* extract contains aistonine.

5. The method of claim 1 wherein the mixture is formed from synthetic flavopereirine and aistonine.

6. The method of claim 1 wherein the mixture is formed from purified flavopereirine and aistonine.

7. The method of claim 1 wherein the subject has a high PSA count, symptoms of BPH (Benign Prostatic Hyperplasia) or symptoms of prostatic intraepithelial neoplasia (PIN).

8. The method of claim 1 wherein the subject has been diagnosed with prostate cancer but has non-aggressive tumors as evidenced by lower Gleason scores.

9. The method of claim 1 wherein the subject is undergoing cancer therapy including surgery, chemotherapy, cryotherapy or radiation.

10. The method of claim 1 wherein administration is oral.

11. The method of claim 10 wherein oral administration is via a tablet or capsule.

12. The method of claim 1 wherein the effective amount is sufficient to induce apoptosis in cancer cells.

13. A composition for treating prostate cancer comprising an effective amount of a mixture of flavopereirine and alstonine, wherein the amount of mixture is sufficient to slow the progression of prostate cancer to a more aggressive stage. lower PSA levels or lower PSA doubling times and Wherein the flavoperine and alstonine are present in the mixture in a ratio of about 3-4 to one.

14. The composition of claim 13 wherein the mixture is formed from natural extracts containing flavopereirine and/or aistonine.

15. The composition of claim 13 wherein the effective amount is sufficient to alleviate the symptoms of BPH (Benign Prostatic Hyperplasia) or lower elevated PSA. Levels.

16. The composition of claim 13 is in a form suitable for oral administration.

17. The composition of claim 16 wherein the form is a tablet or a capsule.

18. The composition of claim 13 wherein the natural extracts are derived from *Pao Pereira* and *Rauwolfia Vomitora*.

19. The composition of claim 14 wherein the *Pao Pereira* extract contains flavopereirine and the *Rauwolfia Vomhitoria* extract contains alstonine.

20. The composition of claim 13 wherein the effective amount is sufficient to induce apoptosis in cancer cells.

21. The composition of claim 13 wherein the flavopereirine and alstonine are synthetic.

22. The composition of claim 13 wherein the flavopereirine and alstonine are in a purified form.

23. A kit for treating prostate cancer or delaying its onset comprising the composition of claim 13 in a dosage form suitable for use in a treatment regimen.

* * * * *